United States Patent [19]

Zablen

[11] 4,438,763
[45] Mar. 27, 1984

[54] AMBULATORY APPARATUS FOR USE IN COMBINATION WITH AN INTRAVENOUS DELIVERY SYSTEM

[76] Inventor: Marshall A. Zablen, 3714 Whitespeak Dr., Sherman Oaks, Calif. 91403

[21] Appl. No.: 404,505

[22] Filed: Aug. 2, 1982

Related U.S. Application Data

[63] Continuation-in-part of Ser. No. 354,503, Mar. 3, 1982.

[51] Int. Cl.³ .......................... A61M 5/14; A45F 5/00
[52] U.S. Cl. .................................... 128/133; 604/179;
224/148; 224/259; 224/265; 128/DIG. 6
[58] Field of Search .......................... 128/DIG. 6, 133;
604/93, 174, 179, 257, 259; 224/148, 185, 187,
189, 259, 265; 2/102

[56] References Cited

U.S. PATENT DOCUMENTS

| | | |
|---|---|---|
| 2,484,383 | 10/1949 | Lee . |
| 2,723,665 | 11/1955 | Goldsmith . |
| 3,120,332 | 2/1964 | White .................................. 224/189 |
| 3,196,872 | 7/1965 | Katz . |
| 3,547,322 | 12/1970 | Dawson . |
| 3,679,107 | 7/1972 | Perrine . |
| 4,087,864 | 5/1978 | La Bove et al. ........................ 2/102 |
| 4,259,187 | 3/1981 | DeFrank et al. . |
| 4,289,129 | 9/1981 | Turner . |

FOREIGN PATENT DOCUMENTS 117055 6/1945 Sweden ............................... 224/185

*Primary Examiner*—C. Fred Rosenbaum
*Assistant Examiner*—Michelle N. Lester
*Attorney, Agent, or Firm*—William W. Haefliger

[57] ABSTRACT

The present invention provides ambulatory support means for use in combination with an intravenous delivery system. The intravenous delivery system typically includes a container for containing a particular solution for delivery into the circulatory system of a patient and a delivering apparatus for delivering the particular solution into the circulatory system of the patient. The intravenous system may include a driving apparatus, such as gravity or a pump, for providing the energy which is required to drive the particular solution from the container through the delivering apparatus into the circulatory system of the patient. In one form of the invention an ambulatory vest includes a back panel and a pair of front panels, the supporting apparatus including a pole and a device for attaching the pole to the vest and device for coupling the bottle of the intravenous system to the pole.

In another form, the invention includes
(a) a relatively rigid support sized to fit adjacent the back of a human patient, and having means thereon to mount an upwardly extending member which in turn is adapted to carry an intravenous liquid container,
(b) a belt section adapted to extend adjacent the abdomen of the wearer, the belt having adjustable connection to lower extent of the support, to provide abdominal support after surgery, and
(c) first flexible strap means connected between the support and the belt so that the strap means then extends upwardly between the belt at the front of the wearer, and upper extent of the support.

In addition, a strap may be provided to retain a fluid container, i.e. a bag or a bottle, snugly to the support. Also, a portable hydraulic pump may be attached to the support for use as a possible fluid driving means.

11 Claims, 7 Drawing Figures

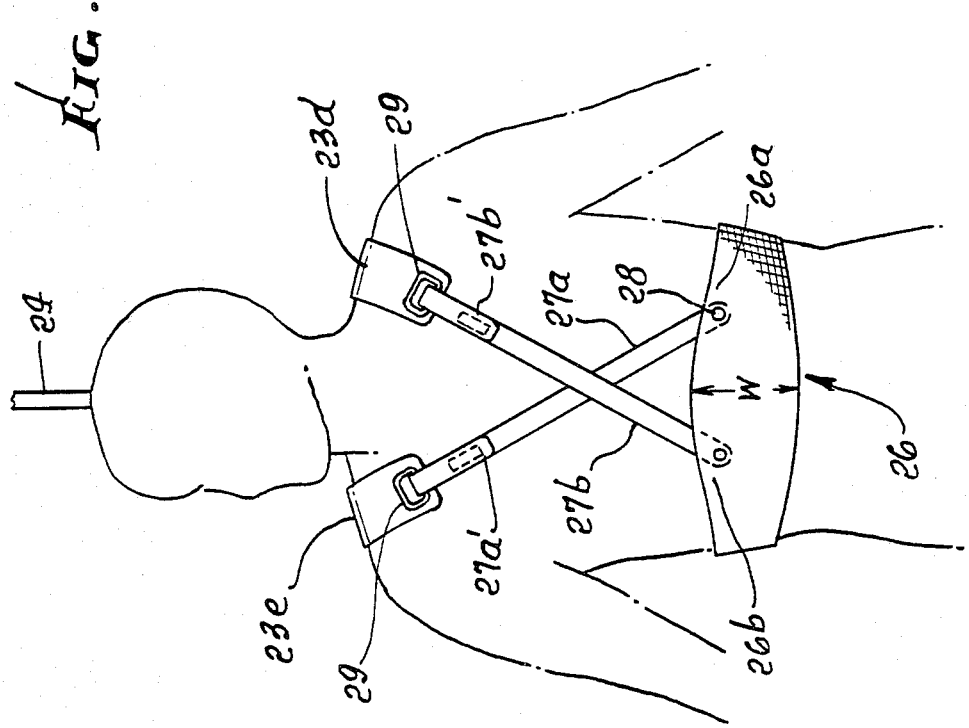
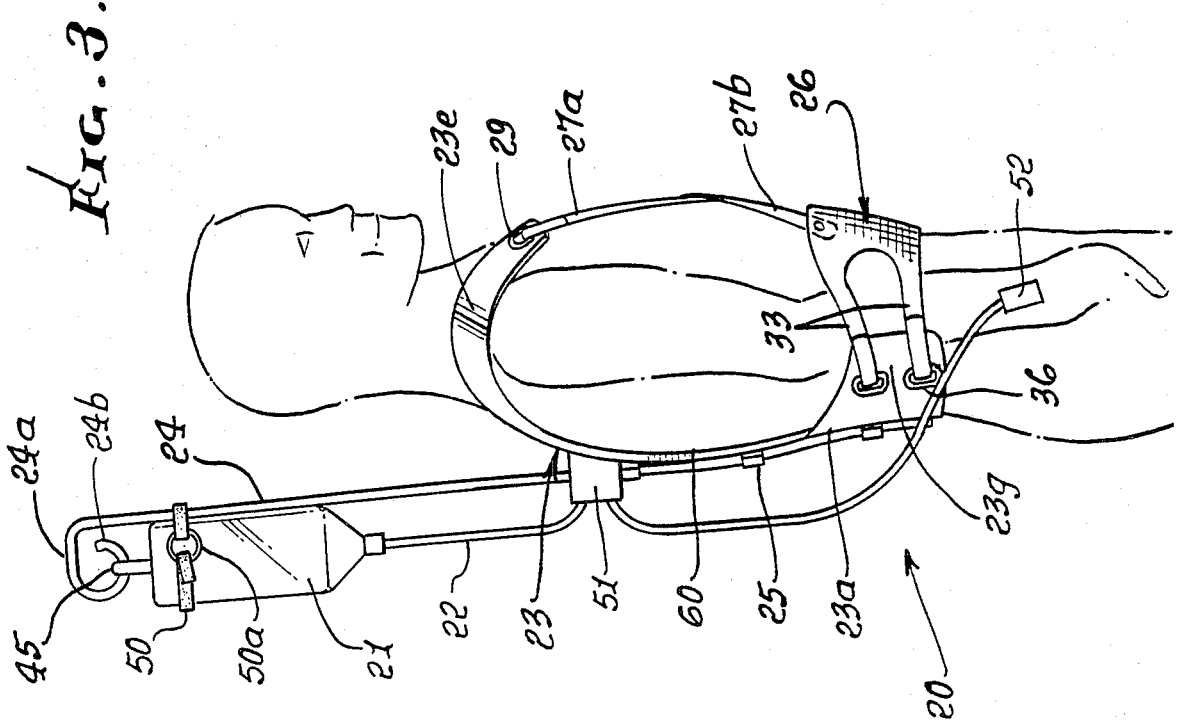

AMBULATORY APPARATUS FOR USE IN COMBINATION WITH AN INTRAVENOUS DELIVERY SYSTEM

BACKGROUND OF THE INVENTION

This application is a continuation-in-part of my prior application Ser. No. 354,503, filed Mar. 3, 1982.

FIELD OF THE INVENTION

The present invention relates to parenteral infusion apparatus and more particularly to patient carried portable apparatus allowing the infusing patient to move with a minimum of restrictions.

DESCRIPTION OF THE PRIOR ART

The patents to Goldsmith U.S. Pat. Nos. 2,723,665 of Nov. 15, 1955 and Dawson 3,547,322 of Dec. 15, 1970 disclose ambulatory intravenous feed devices. However, each device is clumsy and lacks the advantages in construction and use of the present apparatus.

SUMMARY OF THE INVENTION

It is a primary object of the present invention to provide apparatus which enables a patient receiving medication through an intravenous delivery system to walk along the corridors of the hospital without being impeded by the necessity of pushing a movable rack for the intravenous delivery system, such apparatus incorporating important features not suggested by such prior patents.

In accordance with the present invention, there are provided:

(a) a relatively rigid support sized to fit adjacent the back of a human patient, and having means thereon to mount an upwardly extending member which in turn is adapted to carry an intravenous liquid container, (b) a belt section adapted to extend adjacent the abdomen of the wearer, the belt having adjustable connection to lower extent of the support to provide abdominal support after surgery, and (c) first flexible strap means connected between the support and the belt so that the strap means then extends upwardly between the belt at the front of the wearer, and upper extent of the support.

Further, the container may be strap-connected to the support or pole, as will appear.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 3 is a side elevation showing another embodiment;

FIG. 4 is a front view of the FIG. 3 embodiment;

DESCRIPTION OF THE PREFERRED EMBODIMENTS

Figure 1:
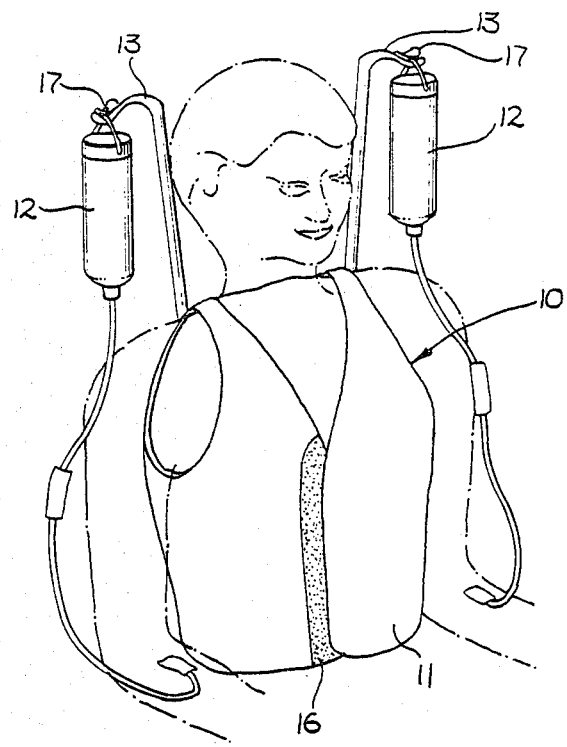
FIG. 1 is a perspective view of an ambulatory vest for use in combination with an intravenous delivery system.

In order to best understand the present invention it is necessary to refer to the following description of its preferred embodiments in conjunction with the accompanying drawings. Referring to FIG. 1 an ambulatory vest 10 may be used in combination with an intravenous delivery system. The ambulatory vest 10 includes a vest 11 which has a back panel and a pair of front panels. Each of the front panels is mechanically coupled to the back panel. The intravenous delivery system 12 includes a container for containing a particular solution for delivery into the circulatory system of a patient and a delivering apparatus for delivering the particular solution into the circulatory system of the patient. The intravenous delivery system 12 also includes a driving apparatus for providing the energy which is required to drive the particular solution from the container through the delivering apparatus into the circulatory system of the patient. The ambulatory vest 10 also includes a supporting apparatus for supporting the intravenous delivery system. The supporting apparatus is mechanically coupled to the vest 11. The supporting apparatus includes a pole 13 and a device for attaching the pole 13 to the vest 11 and a clamp 17 for coupling the bottle of the intravenous delivery system 12 to the pole 13.

Figure 2:
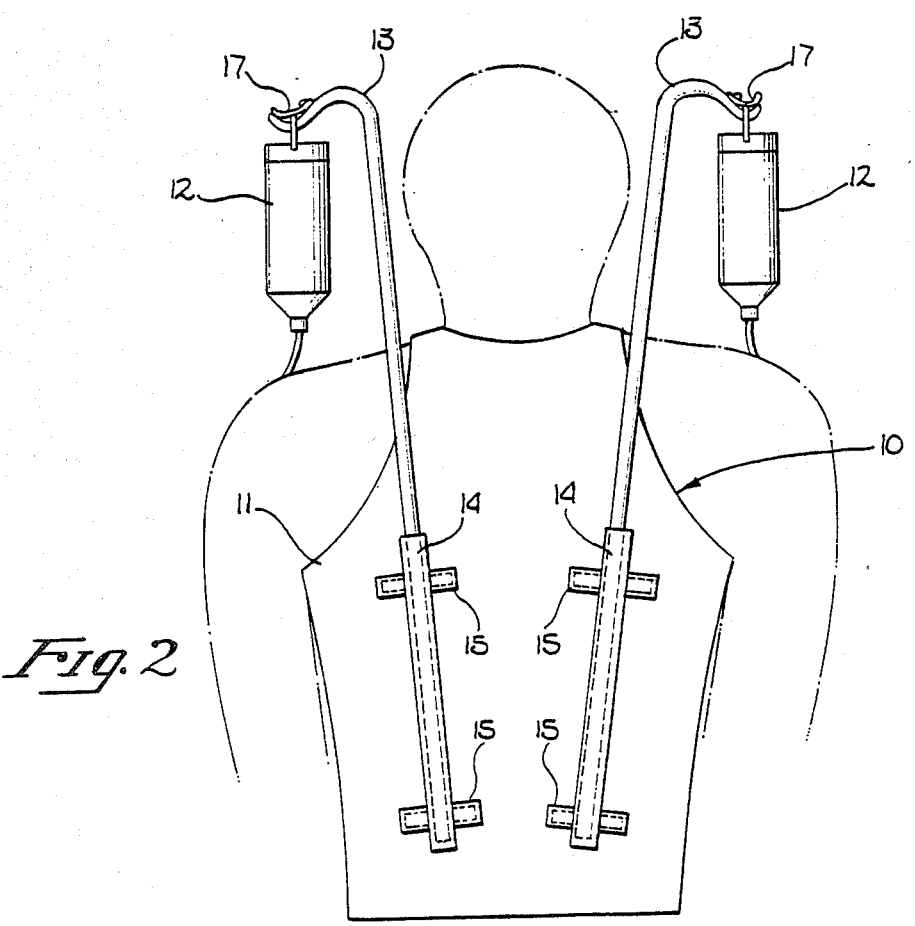
FIG. 2 is a rear elevational view of the ambulatory vest of FIG. 1.
Figure 5:
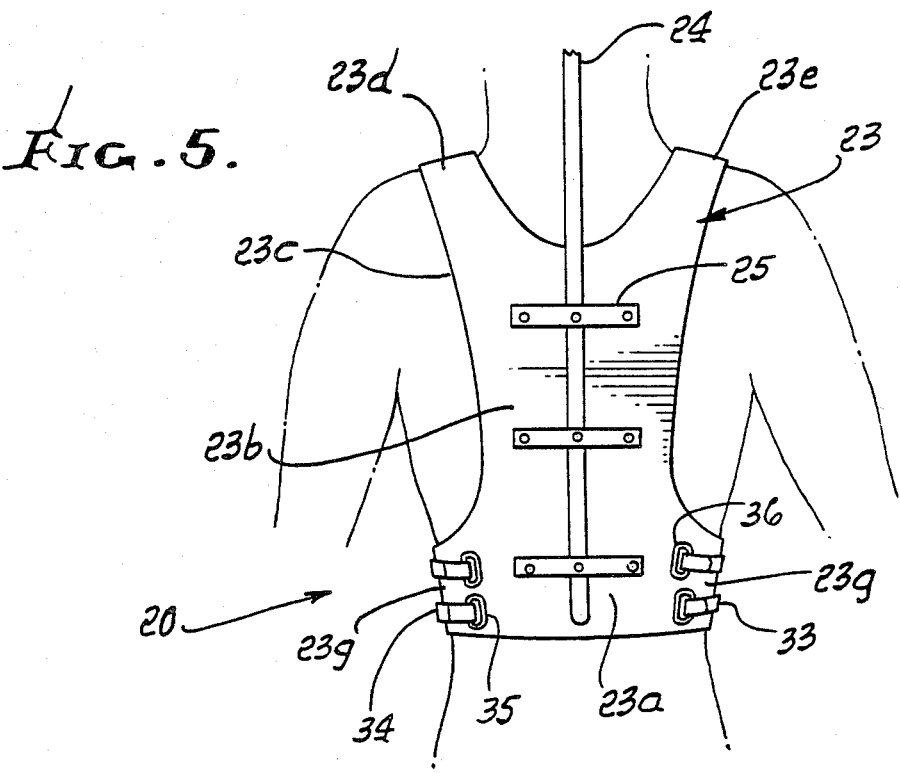
FIG. 5 is a rear view of the FIG. 3 embodiment.
Figure 6:
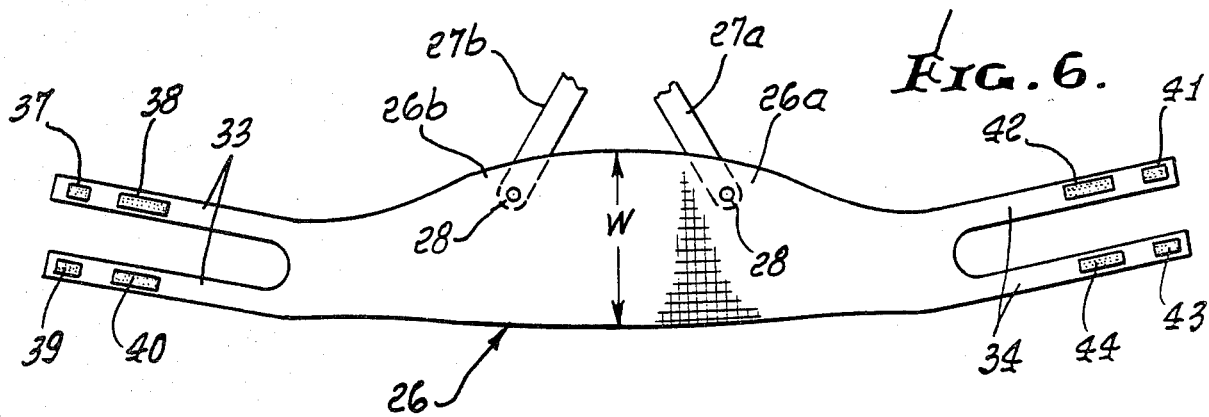
FIG. 6 is an employed frontal view of a belt used in the FIG. 3 embodiment.

Referring to FIG. 2 the device for attaching the pole 13 to the vest 11 includes a hollow sheath 14 and a pair of connecting tabs 15 which are disposed at each end of the sheath 14 and which mechanically couple the sheath 14 to the vest 11.

Referring again to FIG. 1 the container of the intravenous delivery system 12 may be a bottle or plastic bag, and the driving apparatus may consists of maintaining the bottle at a height substantially above the part of the body of the patient at which the output of the delivering apparatus is placed for pressurized gravity feed. This type of intravenous delivery system is a gravity feed system and other types may also be used with the present invention.

In the preferred embodiment the two front panels of the vest 11 may be joined by a VELCRO device and a set of two intravenous delivery systems 12 are used in conjunction with two poles 13 and two devices for attaching the poles 13 to the vest 11.

Referring now to FIGS. 3-6, the equipment 20 for use with an intravenous liquid delivering bottle 21 and delivery line 22 includes a relatively rigid support 23 sized or shaped to fit adjacent the back of a human patient shown at 60. A pump 51 may be connected in series with line 22, and carried by support 23, as shown, to pressurize the fluid delivered via line 22 to the patient's body, at 52. That support may advantageously take the form of a molded plastic sheet having a lower relatively wide portion 23a located adjacent the patient's lower back; a narrowed and upwardly diverging mid-portion 23b extending between upwardly diverging lateral edges 23c and located adjacent the patient's mid and upper back; and left and right hook shaped portions 23d and 23e sized to fit (i.e. hook) over the shoulders of the patient. Since edges 23c are in the shoulder blade area, the patient's outer shoulders are comfortably free for movement, as he or she walks. Accordingly, the support 23 may easily be placed onto the patient, for subsequent attachment in position, despite the carriage by the support of an upwardly extending member, such as pole or standard 24. The latter extends slightly rearwardly from vertical (see FIG. 3), as is desired, due to its rigid attachment at 25 to the mid-portion 23b of the support which also extends upwardly and rearwardly. In general, and as viewed from the side in FIG. 3, the support has S-shape to comfortably conform to the shoulder, mid and upper back, and lower back of the patient.

Subsequent positive attachment of the support to the patient will now be described, and which is accomplished at the front and sides of the patient. For that purpose, a belt section is provided, as for example at 26, to extend adjacent the abdomen of the wearer; and the belt may be several inches wide ($2\frac{1}{2}$–10 inches) as indicated by dimension "$\omega$" to desirably assist in inwardly supporting the patient's abdomen, as after surgery in that area of the body. The belt has adjustable connection to lower extent of the support 23, as will be described.

Figure 7:
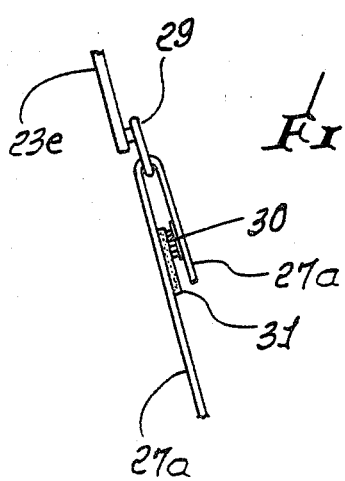
FIG. 7 is an enlarged elevation showing a strap connection.

First flexible strap means is also connected between the belt and support so that the strap means extends upwardly at the front i.e. chest of the patient, thereby to hold the shoulder portions of the support firmly in place on the wearer's shoulders. To this end, the strap means may include first straps 27a and 27b with lower ends connected to horizontally spaced upper portions 26a and 26b of the wide belt, as for example, by rivets 28. The straps extend upwardly in cross-over relation (or straight up) for adjustable connection to the hook-shaped parts 23d and 23e of the support. To that end, the straps may extend through loops 29 on the shoulders 23d and 23e, and then back downwardly to adjustably fasten to the straps. See for example, in FIG. 7, strap end 27a' carrying VELCRO 30, that adjustably connects to elongated VELCRO 31 on strap 27a. See also strap end 27b'. The adjustable connections tension the straps 27a and 27b.

Second adjustable strap means is or are also provided to connect the ends of the belt 26 to opposite lower sides 23g of the support 23 for holding the belt in the position shown. For this purpose, the second strap means may include two parallel straps 33 (or a single strap) integral with or connected to one end of the belt, and two parallel straps 34 (or a single strap) integral with or connected to the opposite end of the belt. See FIG. 6. Such straps fit through loops 35 and 36 pivotally connected to the lower sides of the support, and fold back on themselves, for adjustable connection. See for example VELCRO swatches on the straps, and indicated in FIG. 6 at 37–44. The adjustable connections are made in the same manner as described in respect of FIG. 7.

Referring to FIG. 3, the pole or standard 24 has a rearward projection 24a at an upper level, above the head level of the patient. It forms a loop at 24b to support a bail 45 on the container 21, which contains intravenous liquid, whereby the container hangs downwardly as shown, but protected by the pole from striking the patient's head. A retainer strap 50 on the pole upper extent may be wrapped around the hanging container, to releasably retain it snugly to the pole, as by VELCRO fastener means as described above. Strap 50 has a small ring 50a thereon to pass a strap end that folds back and attaches to the strap, whereby different size bottles may be used. As described, liquid delivery line 22 extends with slack from the bottle to cannulae on the patient's arm, as shown, optionally via pump 51.

From the foregoing, it is seen that the apparatus may be quickly attached to a patient, whose arms are left free for other purposes, as he or she walks. The pole and container are subject to minimum sway, due to pole connection to the support 23, which does not swing with the patient's arm.

The belt and straps may be disposable, and may consist of flexible webbing; also, the support may be made in various sizes, as for children and adults, and is semi-rigid.

From the foregoing it can be seen that an ambulatory vest for use in combination with an intravenous delivery system has been described. It should be noted that the sketches are not drawn to scale and that dimensions of and between the figures are not to be considered significant.

Accordingly, it is intended that the foregoing disclosure and showing made in the drawing shall be considered only as an illustration of the principles of the present invention.

I claim:

1. In combination with an intravenous delivery system, the combination comprising
   (a) a relatively rigid support sheet sized to fit flatly adjacent the lower central back and middle central back of a human patient, and having means thereon mounting an upwardly extending pole member which in turn suspends an intravenous liquid container, said member extending upwardly proximate the medial extent of said sheet, the sheet having a lower relatively wide portion located adjacent the patient's lower back and the patient's sides, a narrowed and upwardly diverging mid-portion extending between upwardly diverging lateral edges and located adjacent the patient's mid and upper back, and terminal left and right hook shaped portions sized to fit over the patient's shoulders,
   (b) a belt section adapted to extend adjacent the abdomen of the wearer, the belt section having adjustable connection to lower side extends of the support, the belt section having a mid-portion of a vertical width generally to cover the patient's abdomen and extending at a level to provide abdominal support to the patient, after surgery, and
   (c) first flexible strap means connected between the support sheet and the belt so that the strap means then extends upwardly between the belt at the front of the wearer patient, and upper extent of the support, proximate the shoulders of the wearer patient,
   (d) whereby the patient may then move about with his or her arms free of constraint by the support.

2. The combination of claim 1 wherein said support comprises a relatively rigid plastic sheet which is vertically elongated with S-shape when viewed sidewardly to fit adjacent the lower and upper back of the human patient, the two hook-shaped portions attached to said strap means.

3. The combination of claim 2 wherein said support sheet has edges which extend downwardly from said hook shaped portions proximate the shoulder blade area of the human wearer.

4. The combination of claim 1 including second adjustable strap means connecting the belt section to opposite sides of said support, the belt mid-portion having a width between $2\frac{1}{2}$ and 10 inches.

5. The combination of claim 4 wherein said second strap means includes straps attached to opposite end portions of said belt, and which fit through loops on said support to fold back for adjustable connection to the straps.

6. The combination of claim 2 wherein said first strap means includes first straps connected to horizontally spaced portions of the belt and which extend upwardly in cross-over relation for adjustable connection to said hook shaped portions of the support.

7. The combination of claim 6 wherein said first straps fit through loops on said hook shaped portions of the support, and fold back for adjustable connection to the straps.

8. The combination of claim 1 including a pump carried by said support for connection in series with a liquid delivery line from said container.

9. The combination of one of claims 1, 7 and 8 including a rearward projection on the member a tan upper level for supporting a container for said intravenous fluid, and an additional strap located on said member to releasably retain said container to said member.

10. The combination of claim 1 wherein support consists of molded plastic material, and the belt and strap means consist of flexible material and are disposable.

11. The combination of claim 1 including said container in the form of a bag, and strap means to exert pressure on the bag tending to pressurize the liquid therein for delivery via a line to the patient.

* * * * *